United States Patent [19]

Pepin et al.

[11] Patent Number: 5,430,291
[45] Date of Patent: * Jul. 4, 1995

[54] X-RAY CT MEASUREMENT OF FRACTURE WIDTHS AND FRACTURE POROSITY IN RESERVOIR CORE MATERIAL

[75] Inventors: Gregory P. Pepin, Sugar Land; Robert M. Moss, Houston, both of Tex.

[73] Assignee: Texaco Inc., White Plains, N.Y.

[ * ] Notice: The portion of the term of this patent subsequent to Oct. 25, 2011 has been disclaimed.

[21] Appl. No.: 124,688

[22] Filed: Sep. 22, 1993

Related U.S. Application Data

[63] Continuation-in-part of Ser. No. 877,511, May 1, 1992, abandoned.

[51] Int. Cl.⁶ .................. G01N 23/10; G01V 5/00
[52] U.S. Cl. .................................. 250/255; 378/4
[58] Field of Search .............. 250/253, 255; 378/4, 378/51, 53; 73/153

[56] References Cited

U.S. PATENT DOCUMENTS

| | | | |
|---|---|---|---|
| 4,722,095 | 1/1988 | Muegge et al. | 378/4 |
| 4,782,501 | 11/1988 | Dixon, Jr. | 378/4 |
| 4,799,382 | 1/1989 | Sprunt et al. | 73/153 |
| 4,868,751 | 9/1989 | Dogru et al. | 364/422 |
| 4,884,455 | 12/1989 | Vinegar et al. | 73/798 |
| 4,982,086 | 1/1991 | Withjack | 250/255 |
| 5,036,193 | 7/1991 | Davis, Jr. et al. | 250/255 |
| 5,048,328 | 9/1991 | Puri | 73/153 |
| 5,164,672 | 11/1992 | Gilliland et al. | 324/376 |

Primary Examiner—Constantine Hannaher
Assistant Examiner—Edward J. Glick
Attorney, Agent, or Firm—James L. Bailey; Kenneth R. Priem; Russell J. Egan

[57] ABSTRACT

A method for determining the widths of fractures in reservoir earthen cores utilizes a series of CT X-ray scans which are translated into an estimated porosity image. A region of interest within the image is selected and a frequency histogram of the porosity distribution is created. The contribution of the fracture widths to the pore volume is determined from the histogram.

2 Claims, 8 Drawing Sheets

X-RAY CT MEASUREMENT OF FRACTURE WIDTHS AND FRACTURE POROSITY IN RESERVOIR CORE MATERIAL

CROSS REFERENCE TO RELATED APPLICATIONS

This is a continuation-in-part of our patent application Ser. No. 07/877,511 filed May 1, 1992 now abandoned.

BACKGROUND OF THE INVENTION

1. The Field of the Invention

The present invention pertains to the use of X-ray computed tomography (CT) to measure widths of fractures and their contributions to the overall pore volume in fractured reservoirs.

2. The Prior Art

Previous methods for measuring fracture widths in core material required analysis of thin core segments. These methods have had the obvious difficulties associated with limited sampling. Examples of prior art methods for examining earth cores may be found in U.S. Pat. Nos. 4,982,604; 5,036,193; and 5,058,425, the disclosures of which are incorporated herein by reference.

SUMMARY OF THE INVENTION

The present invention pertains to a method for determining the widths of fractures in reservoir earthen core material through the use of X-ray CT measurements. A series of CT scans are translated to number images to form an estimated porosity image in Hounsfield Units. A region of interest within the image is selected and a frequency histogram of the porosity distribution is created. The fractional contribution to the pore volume is determined from the histogram.

BRIEF DESCRIPTION OF THE DRAWINGS

The present invention will now be described, by way of example, with reference to the accompanying drawings in which.

DETAILED DESCRIPTION OF THE PREFERRED EMBODIMENT

For purposes of this discussion, the term "fracture porosity" will be used to describe the contribution of fractures to the total pore volume.

The present invention utilizes the following procedure to determine the contribution of fracture volume to the pore volume:

(1) First, a series of CT scans are made of the earthen core material, FIGS. 1A to 1D. The material can be scanned in an "as received" native state (at ambient temperature and pressure conditions) or in a confined state, i.e. in a core barrel under confining stresses similar to those the core would have experienced in the reservoir.

(2) The images are then transferred from the CT scanner to an image analysis computer for processing.

(3) The CT number image, which is displayed in Hounsfield Units (HU), is translated into an estimated porosity image. The equations that relate porosity to the CT number image are given below:

$$H_c = (1-\phi)*H_r + \phi*(S_f*H_f + S_g*H_g)$$

$$S_f + S_g = 1$$

where
$H_c$ = CT number (Hounsfield Units) of the core
$H_r$ = CT number of the zero porosity rock matrix
$\phi$ = core porosity
$H_f$ = CT Number of the fluid in core
$H_g$ = CT Number of the gas in the core
$S_f$ and $S_g$ = the fractional saturations of the fluid and the gas in the core, respectively.

It is well known that a CT Number image is a pictorial representation of a 2-dimensional array of CT numbers displayed by assigning a color or grayscale intensity to each location in the array according to the value of the CT Number at that location. The resulting color or grayscale picture is displayed on some medium, such as a computer screen or on paper. Because each pixel in the image represents a number, the image can be transformed mathematically from a CT Number image to an image of other quantities, such as porosity, by using equations, such as that described herein. Each pixel (array location) is acted on separately using the transform to create a new array of porosity values that can then be assigned local colors/grayscale to be displayed as a porosity image.

The total fluid in the core is used in the equation above since brine and oil that fill a core in its natural state have nearly the same CT numbers. A more general equation can be used, if necessary, to separate the fluid into both brine and oil contributions.

In order to employ the present invention with only a single set of scans, several assumptions must be made about the gas and fluid saturations of the core. For native state cores, their being fluid-filled is a reasonable assumption ($S_f = 1$) while for cleaned cores, being gas-filled is a reasonable assumption ($S_g = 1$).

Figure 1A:
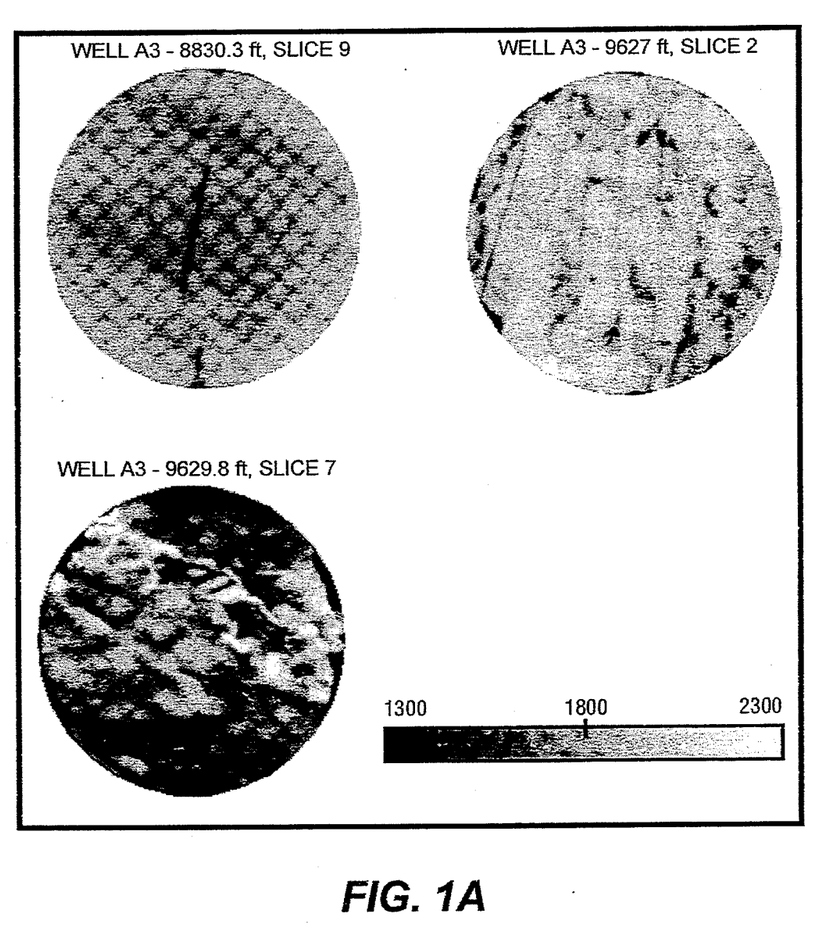
FIG. 1A to 1D are X-ray CT images of the samples used to develop the present invention.
Figure 1B:
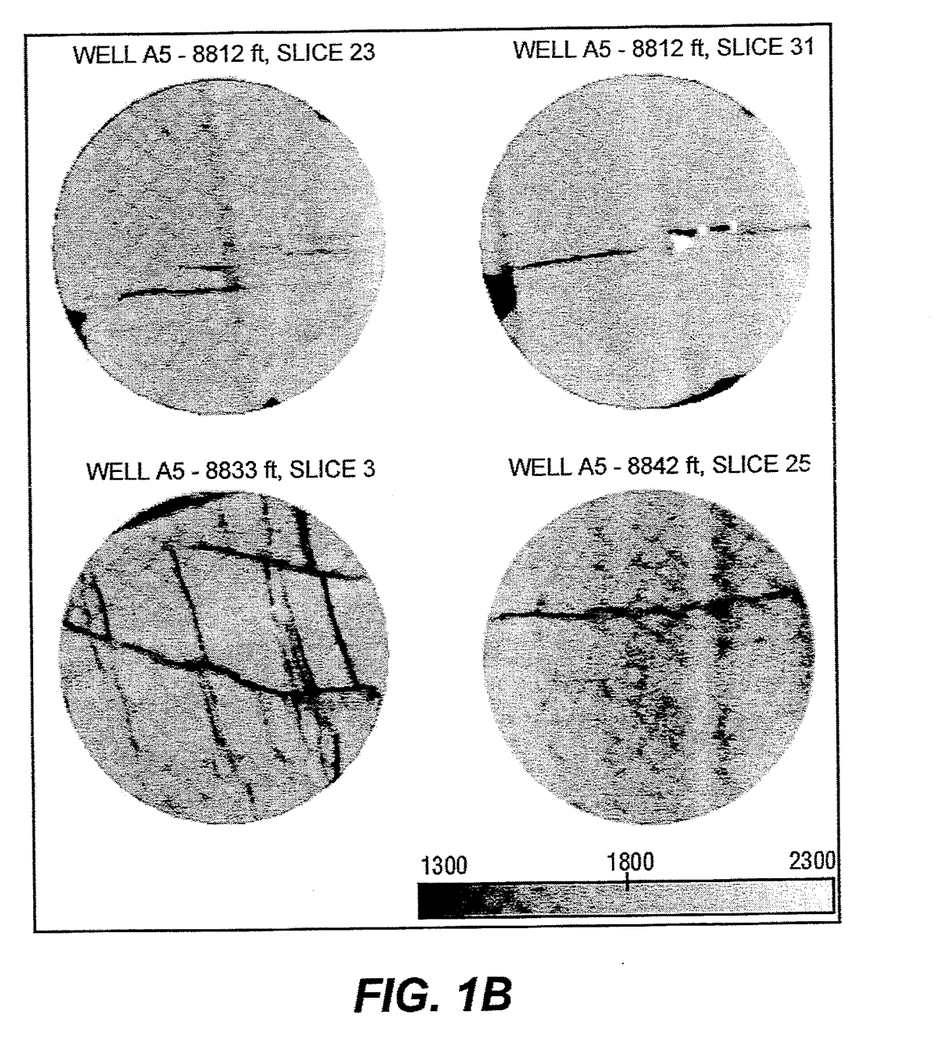
Figure 1C:
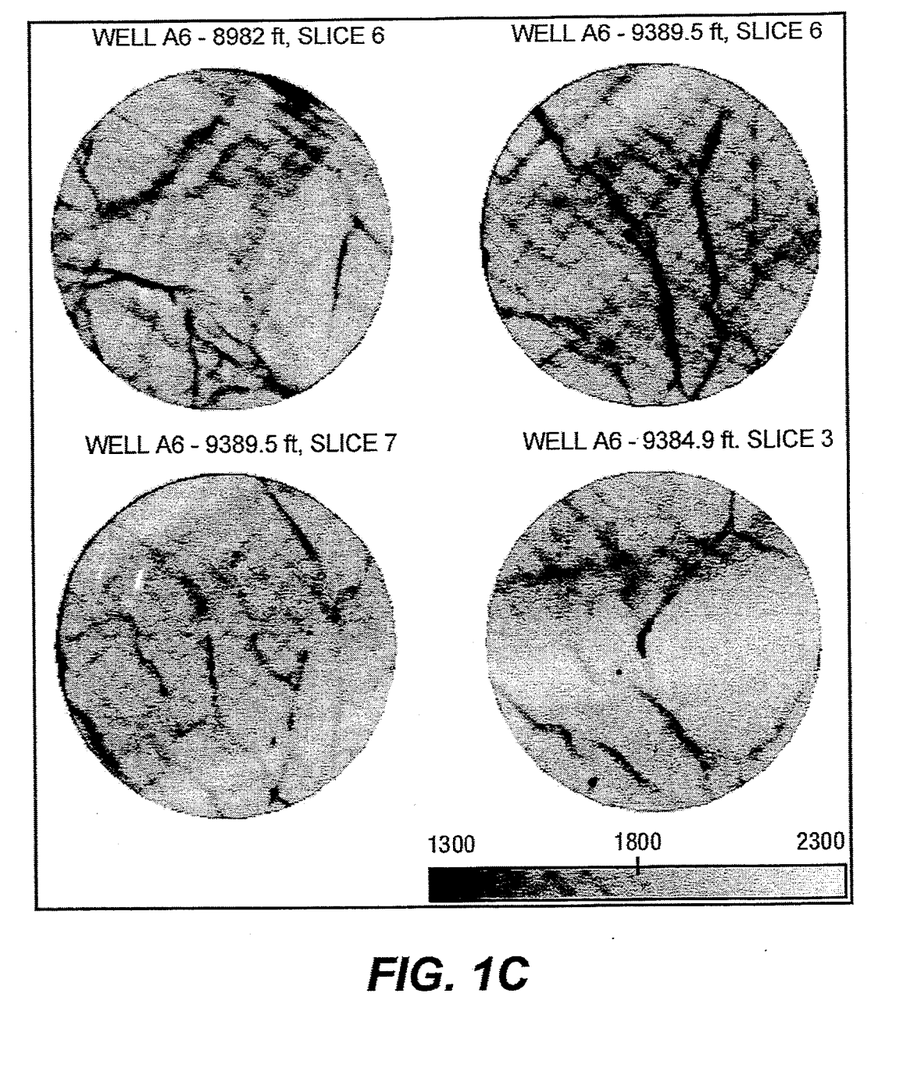
Figure 1D:
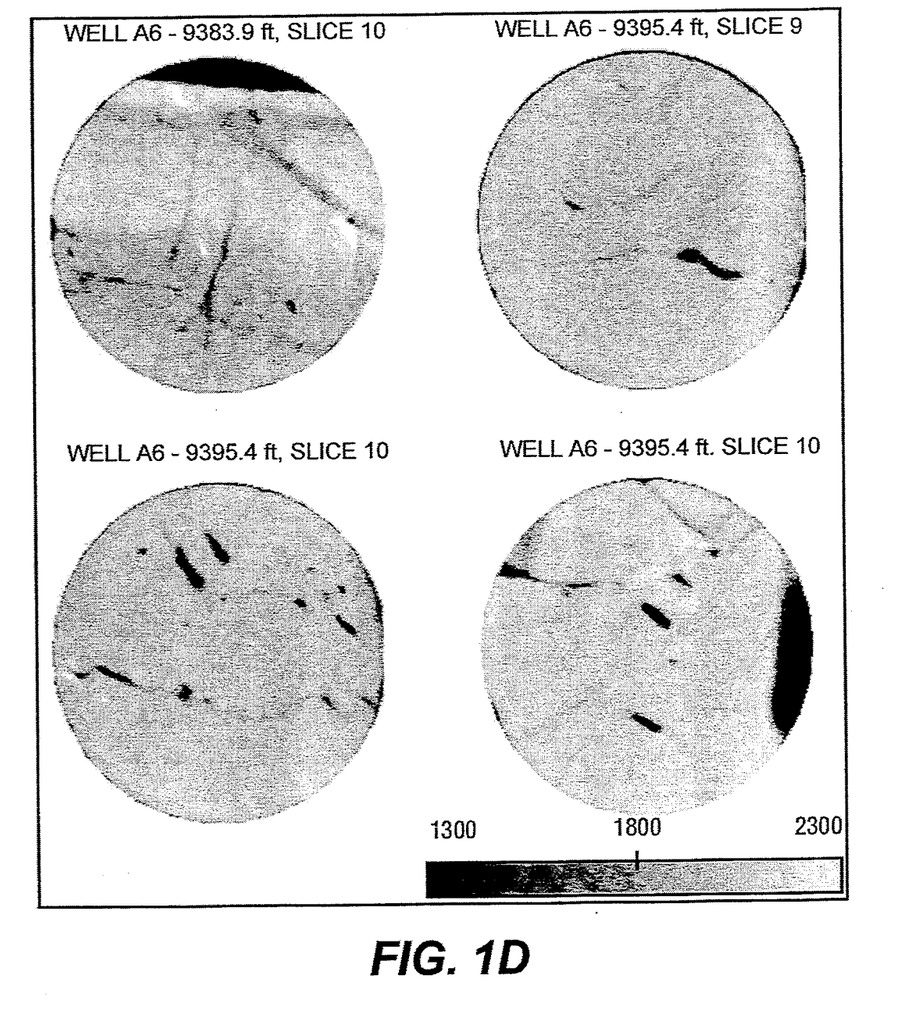
Figure 2:
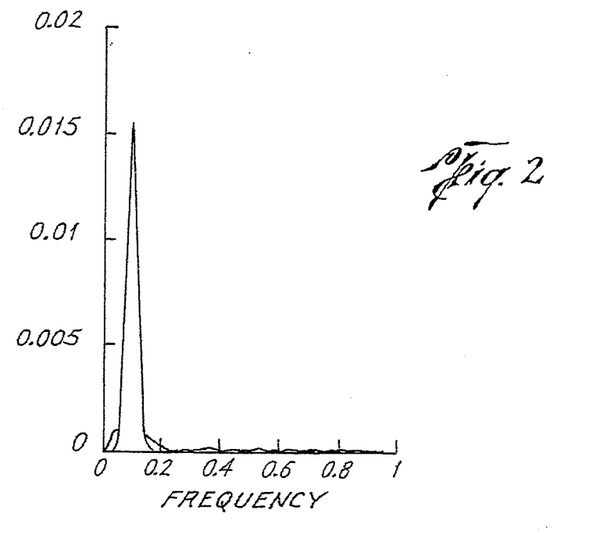
FIG. 2 is a frequency histogram.

(4) After converting the CT number image to a porosity image, a region of interest within the image is selected and a frequency histogram of the porosity distribution within that region is created. FIG. 2 shows a frequency histogram of the porosity distribution of FIG. 1d, the image in the upper left corner.

Note that the frequency histogram is normalized such that the area under the histogram is 1. The tail in the frequency histogram at high porosity is the contribution due to the fracture system. The large peak is the contribution of the matrix component.

(5) The shape of the frequency histogram for a fractured core can generally be described as a peak caused by the intergranular matrix component and a broad scattering of high porosity areas that are a result of the fractures (fractures will have very high local porosity). A gaussian distribution is fit to the peak in the frequency histogram caused by the matrix component.

(6) The gaussian distribution that describes the matrix component has both a mean and a standard deviation (which is an estimate of the amount of local variability of the porosity within the image). The fracture system is detectable as excess number of points above the primary fit at a distance of 2.5 to 3 standard deviations from the mean. Three standard deviations are used since this cutoff provides a 99% confidence level that the contribution is a result of fractures.

(7) The fractional contribution to the pore volume from the fractures is determined from the ratio of the area under the frequency histogram that has been identified as fracture to the total area under the frequency histogram. For the samples used in developing this technique, this ranged from 0.5% to 17%.

The present invention can be utilized to determine the fracture width by:

(1) Creating an image of only the fracture porosity by using the criterion of steps (1) to (6) above. This is done by discarding all data below the porosity cutoff. The fracture system is detectable as an excess number of points above the peak of the histogram at a distance of 2.5 to 3 standard deviations from the mean.

Figure 3A:
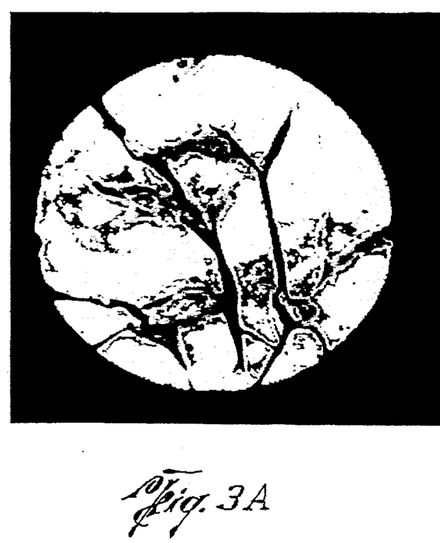
FIGS. 3A and B are matrix and fracture images, respectively.
Figure 3B:
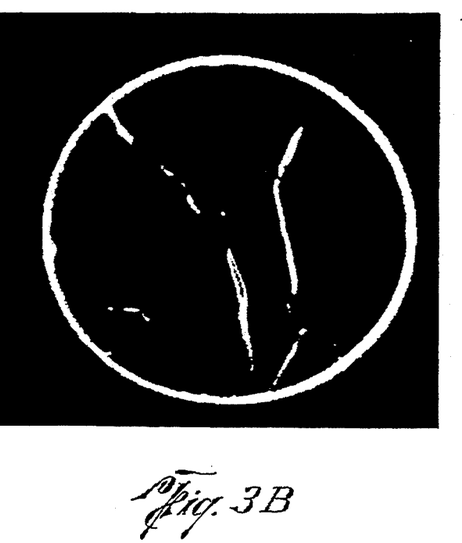

(2) The image is transformed back to a CT number using Equation 1 (for example see FIGS. 3A and 3B).

(3) The resulting image contains CT data about only the fractures. The "matrix" part of the image has been discarded, as described in (1). The range of local CT numbers in each pixel that contains a fracture ranges from a minimum value (either 0 if the core is fluid filled or −1000 if the core is gas filled) where the pixel contains a large fracture that completely fills the pixel, to a maximum value that corresponds to a pixel that contains mostly matrix with only a very small contribution from the fracture. The minimum value corresponds to the fluid that fills the open fractures. The maximum value corresponds to the CT number associated with the porosity cutoff used to determine whether the pixel contains matrix or fracture. The fracture image is still an array of numbers and thus can be transformed using a mathematical equation. The fracture image is rescaled from 0% fracture (no fracture) to 100% fracture (large, open fracture that fills the pixel) where 0% corresponds to the maximum value from the CT number fracture image and 100% corresponds to the fluid that fills the fracture.

Figure 4:
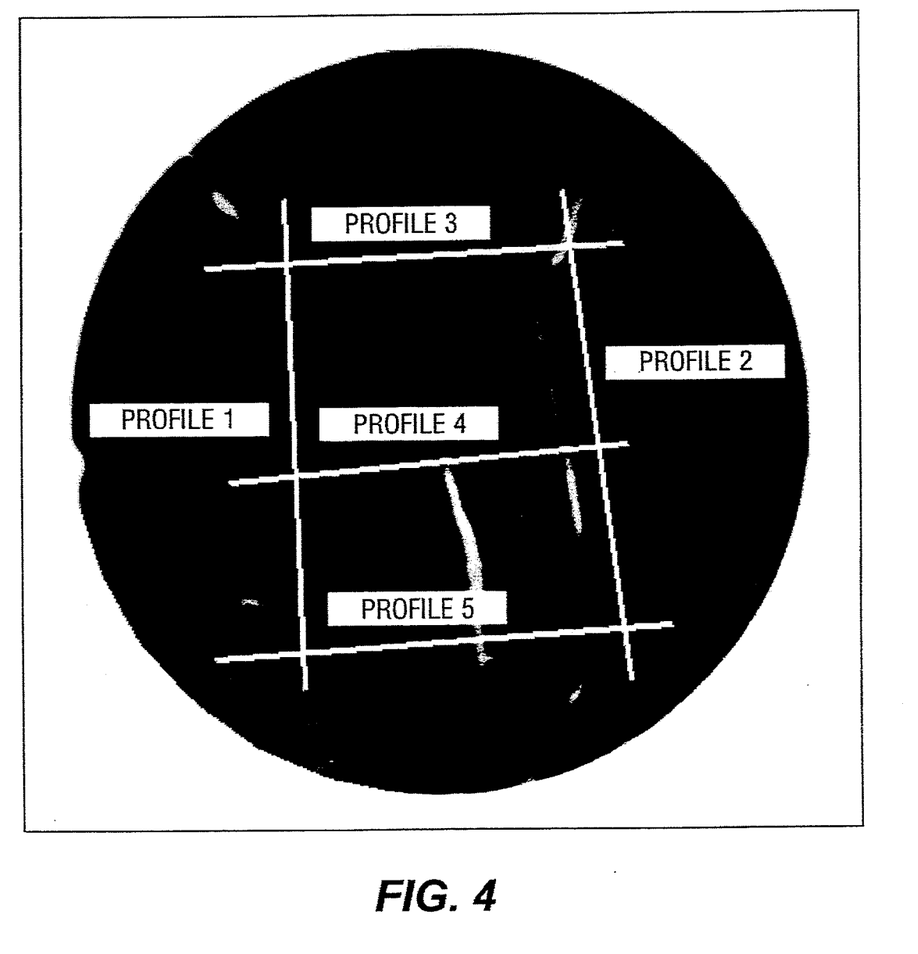
FIG. 4 is a fracture image with profile lines indicating where fracture widths were measured.
Figure 5A:
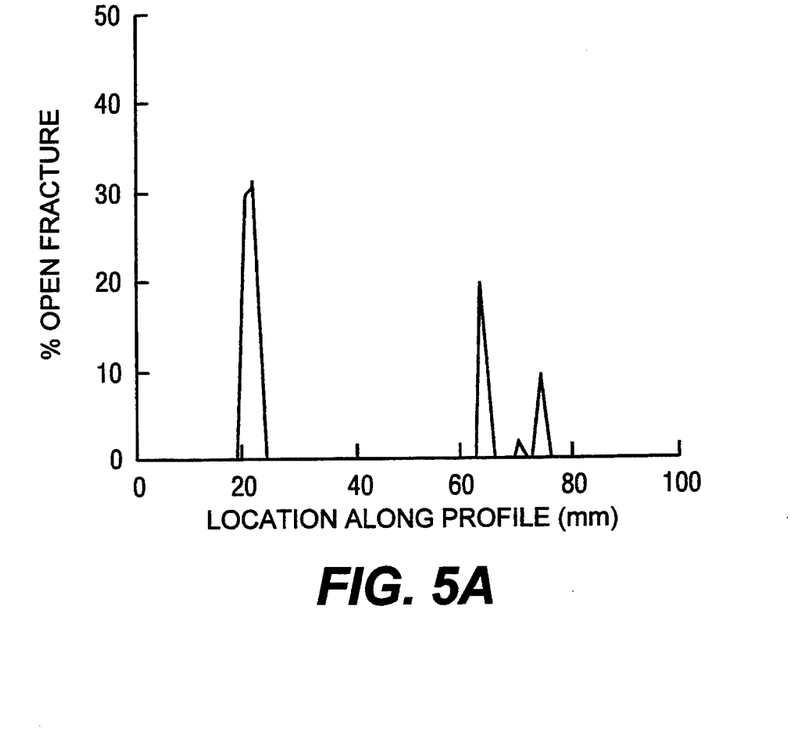
FIG. 5A and 5B are plots of fracture openings.
Figure 5B:
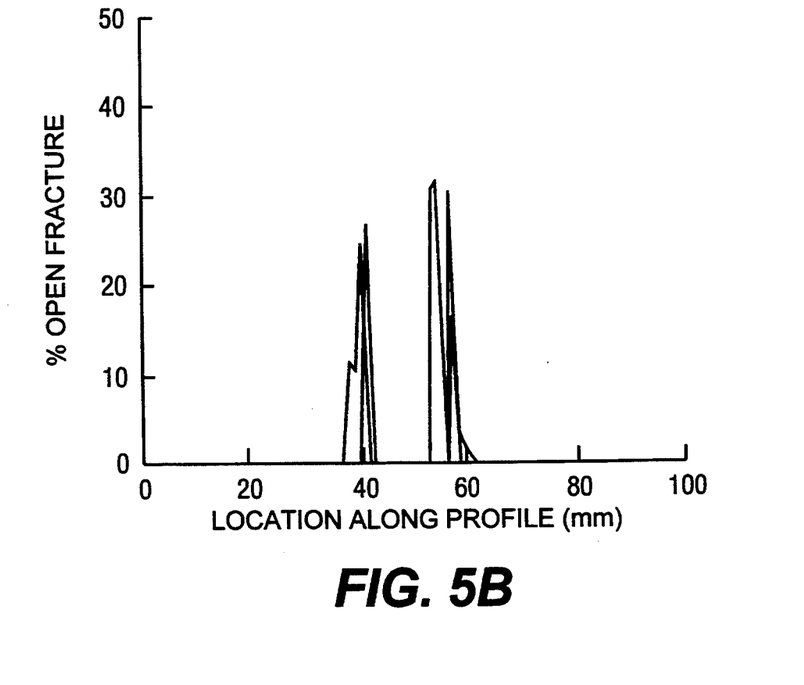

(4) The CT number values are plotted along the region across the image as a function of location along the profile (for example see FIGS. 4 and 5A and 5B).

Figure 6:
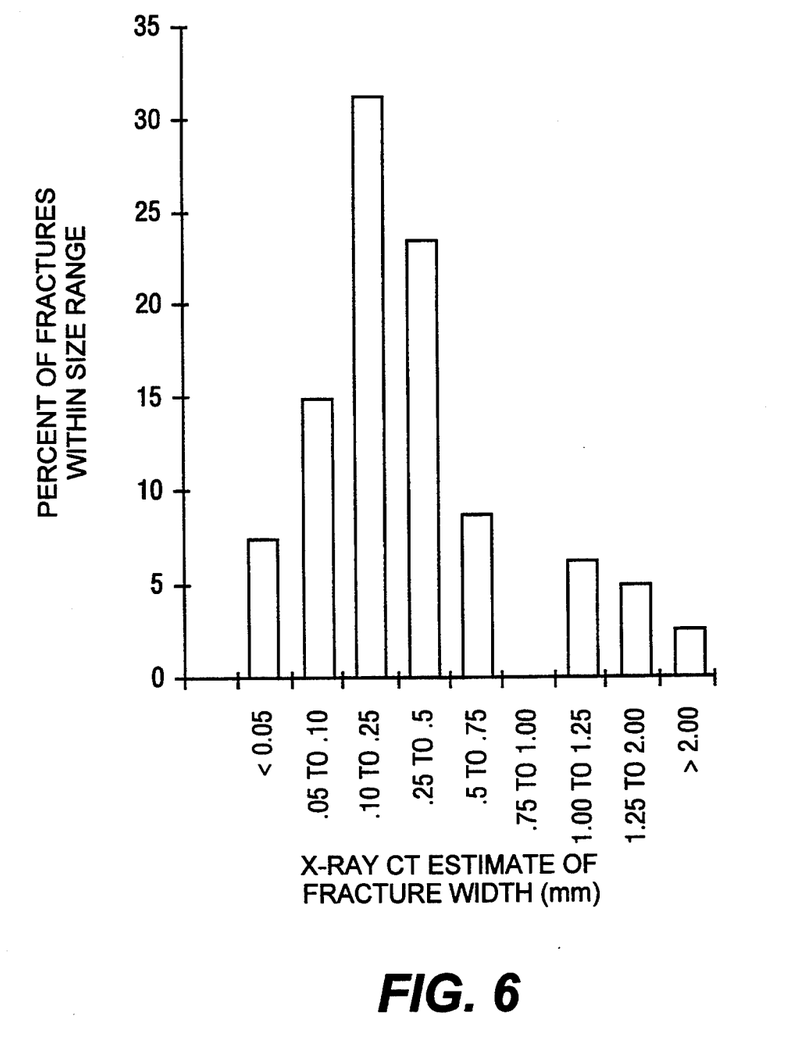
FIG. 6 is a frequency histogram of fracture widths with a mean fracture width of 0.52 mm.

(5) The full width at half maximum is determined for the fracture and multiplied by the height of the peak, which gives the fraction of voxel filled by fracture to obtain an estimate of the fracture width. FIG. 6 shows an example of the resulting distribution from several samples to test the technique.

Estimates of fracture widths and of pore volume due to fractures made using X-ray CT images of core material from three wells (hereinafter identified as A3, A5, and A6) were used. The fraction of pore volume within fractures was estimated using a method that uses CT images to estimate the relative contribution of different pore systems in dual porosity core. For the present analysis, the fracture system was taken as the second "pore" system. Fractures were defined to be those areas whose porosity was greater than three standard deviations higher than that of the primary (mean) porosity for a scan location, as estimated from the x-ray CT data. The fracture width was estimated using the apparent width of the fracture, corrected using a partial volume analysis. The partial volume analysis takes into account the fraction of a voxel containing fracture and the fraction containing rock. The apparent width of the fracture was adjusted by the partial volume of the voxel filled by the fracture. This analysis results in an estimate of the upper limit of the fracture opening.

The fracture porosity was estimated to range from a minimum of 0.5% to a maximum of 17%, with fracture porosity from most samples ranging from 1% to 5%. The estimated fracture widths ranged from less than 0.05 mm to greater than 2 mm with the majority of the fractures having widths less than 0.75 mm. Also, it is important to note that this work was performed on unstressed cores. Placing the cores under confining pressure will result in a decrease in fracture width and fracture porosity.

The biggest complication in estimating the fracture width from CT images results from the finite volume resolution of the CT scanner. A CT image is a 2-dimensional representation of a three dimensional measurement with each 0.25 mm square pixel representing a volume of 0.25 mm×0.25 mm×2 mm (0.125 mm$^3$). Only a very large fracture will completely fill this volume. In most cases the volume will be at least partially filled with the rock matrix. In addition, a narrow fracture that cuts across the core at a high angle will appear wider than it actually is and, in fact, may appear wider than a large fracture that runs parallel to the core axis, perpendicular to the scan plane. These facts must be accounted for in estimating the fracture width.

If the fracture is large enough to be visible in several images along the core axis, its angle with respect to the core axis can be calculated and used to correct the fracture width. In the present dataset, fractures were often visible in only one or two scans due to either the extent of the fracture or to the low scanning frequency along the core axis. To overcome this lack of fracture angle data, a partial volume calculation was used to correct the fracture width, meaning that the measured width was multiplied by the fraction of the volume element (voxel) estimated to be taken up by the fracture.

For images containing large numbers of fractures, several profiles were calculated in order to measure widths of all fractures. Some fractures were included more than once (at different locations along the fracture) by this procedure. This increases the chance of detecting the maximum opening for each fracture.

The present invention may be subject to many modifications and changes within the abilities of those skilled in the art without departing from the spirit of essential characteristics of the present invention. Therefore the above description should be taken as illustrative and not restrictive as to the scope of the invention as defined by the appended claims.

We claim:

1. A method to determine the contribution of fracture volume to the pore volume, comprising the steps of:
   (1) providing test cell means to contain an earthen core;
   (2) placing an earthen core in said test cell means;
   (3) pressurizing the test cell means to simulate reservoir conditions;
   (4) providing a computed tomographic (CT) scanner for scanning the earthen core and generating an image for each scan;
   (5) making a series of CT scans of said earthen core;
   (6) transferring the scan images of the CT scanner to an image analysis computer for processing;
   (7) translating an image from said image analysis computer, which is displayed in Hounsfield Units (HU), into an estimated porosity image by the following equations:

$$H_c = (1-\phi)*H_r + \phi*(S_f*H_f + S_g*H_g)$$

$$S_f + S_g = 1$$

where
- $H_c$ = CT number (Hounsfield Units) of the core
- $H_r$ = CT number of the zero porosity rock matrix
- $\phi$ = core porosity
- $H_f$ = CT number of the fluid in core
- $H_g$ = CT number of the gas in the core
- $S_f$ and $S_g$ = the fractional saturations of the fluid and the gas in the core, respectively;

(8) selecting a region of interest within the porosity image and creating a frequency histogram of the porosity distribution within that region of interest;

(9) describing a gaussian distribution the shape of which approximates the peak of the frequency histogram which is caused by the matrix component of said earthen core;

(10) obtaining from said gaussian distribution describing the matrix porosity both a mean and a standard deviation and identifying fractures as any areas under the frequency histogram whose porosity is more than three standard deviations above the mean of the gaussian distribution; and (11) determining the contribution to the pore volume of the fractures from the ratio of the area under the frequency histogram that has been identified as fracture to the total area under the porosity histogram.

2. The method for determining fracture width within a core sample, comprising the steps of:

(1) containing an earthen core to be tested in a test cell;

(2) testing said earthen core with tomographic means;

(3) generating signals from said tomographic means corresponding to said testing;

(4) processing said signals to create an image of only fracture porosity from a gaussian distribution of the matrix porosity by identifying those areas exceeding a standard deviation from said distribution;

(5) transforming the image back to a CT number image using the equations:

$$H_c = (1-\phi)*H_r + \phi*(S_f*H_f + S_g*H_g)$$

$$S_f + S_g = 1$$

where
- $H_c$ = CT number (Hounsfield Units) of the core
- $H_r$ = CT number of the zero porosity rock matrix
- $\phi$ = core porosity
- $H_f$ = CT number of the fluid in core
- $H_g$ = CT number of the gas in the core
- $S_f$ and $S_g$ = the fractional saturations of the fluid and the gas in the core, respectively;

(6) rescaling the CT number by either 0 (for an assumed fluid-filled core) or $-1000$ (for an assumed gas-filled core) to a maximum CT number defined as fracture, the lower value (0 or $-1000$) assuming that the rescaled location is only fracture while the maximum value implies the rescaled location contains only matrix;

(7) plotting the rescaled values along a linear profile across the CT number image as a function of location along the profile such that a fracture shows up as a peak in said profile; and (8) determining the width of the fracture by multiplying the width at half maximum of the peak by the maximum height of the peak.

* * * * *